(12) United States Patent
Hirschel et al.

(10) Patent No.: US 8,562,570 B2
(45) Date of Patent: Oct. 22, 2013

(54) LOCK APPLIED TO SETTING AND PRIMING FUNCTION AFTER DISPENSING THE LAST DOSE

(75) Inventors: Juerg Hirschel, Aarau (CH); Ulrich Moser, Heimiswil (CH); Markus Tschirren, Kirchberg (CH); Eric Hattler, Solothurn (CH)

(73) Assignee: TecPharma Licensing AG, Burgdorf (CH)

( * ) Notice: Subject to any disclaimer, the term of this patent is extended or adjusted under 35 U.S.C. 154(b) by 830 days.

(21) Appl. No.: 12/632,449

(22) Filed: Dec. 7, 2009

(65) Prior Publication Data

US 2010/0200787 A1 Aug. 12, 2010

Related U.S. Application Data

(63) Continuation of application No. PCT/EP2008/004448, filed on Jun. 4, 2008.

(30) Foreign Application Priority Data

Jun. 8, 2007 (DE) .......................... 10 2007 026 555

(51) Int. Cl.
*A61M 5/00* (2006.01)
(52) U.S. Cl.
USPC .......................... 604/207; 604/187; 604/110
(58) Field of Classification Search
USPC .......................... 604/110, 187, 207, 208, 211
See application file for complete search history.

(56) References Cited

U.S. PATENT DOCUMENTS

| 7,857,791 B2 * | 12/2010 | Jacobs et al. ................. 604/224 |
| 2003/0050609 A1 * | 3/2003 | Sams ............................ 604/208 |
| 2004/0068236 A1 | 4/2004 | Moller et al. |
| 2007/0016142 A1 | 1/2007 | Burren et al. |
| 2008/0183138 A1 | 7/2008 | Moser et al. |

FOREIGN PATENT DOCUMENTS

| DE | 10 2005 044 096 | 11/2006 |
| EP | 1 683 537 | 7/2006 |
| WO | WO 2005097240 A1 * | 10/2005 |

* cited by examiner

*Primary Examiner* — Laura Bouchelle
(74) *Attorney, Agent, or Firm* — Dorsey & Whitney LLP; David E. Bruhn, Esq.

(57) ABSTRACT

An injection device having a safeguard for preventing a filling or adjusting motion of the injection device when a prescribed dispensing motion has been performed, the injection device including an adjusting element and/or a filling element, a blocking mechanism including a first blocking element and a second blocking element, the blocking mechanism allowing a motion of the adjusting and/or filling element in a release position and preventing the motion in a blocking position, and a piston rod including a block trigger element that can bring one of the blocking elements into interaction with the other blocking element thereby creating a blocking position at a prescribed insertion position to cause a blocking of at least one of the adjusting element and/or the filling element.

10 Claims, 5 Drawing Sheets

LOCK APPLIED TO SETTING AND PRIMING FUNCTION AFTER DISPENSING THE LAST DOSE

CROSS-REFERENCED RELATED APPLICATIONS

This application is a continuation of International Patent Application No. PCT/EP2008/004448 filed Jun. 4, 2008, which claims priority to German Patent Application No. DE 10 2007 026 555.9 filed Jun. 8, 2007, the entire contents of each are incorporated herein by reference.

BACKGROUND

The present invention relates to devices for injecting, dispensing, administering, delivering or infusing a substance, and to methods of making and using such devices. More particularly, it relates to an injection device with a mechanism for preventing dispensing when the injection device, a component thereof or an auxiliary component therefor is empty. For example, in some embodiments, the present invention relates to an injection device with a feature for preventing or avoiding a control operation via which control operation a user normally believes a dispensing operation has been actuated or is actuated, thereby preventing or avoiding the user's misapprehension that a dose actually has or is being dispensed.

By virtue of another aspect, the present invention relates to an injection device with a lock for preventing a priming or setting movement of the injection device when one or more predefined dispensing movements of a plunger rod or threaded rod have been effected, e.g. if a predefined dose or quantity has been dispensed, if there is not another dose left, or there is an insufficient quantity for a dose, etc.

SUMMARY

In some embodiments, the present invention relates to a so-called fixed-dose injection device or injection pen used for dispensing a dose that is usually based on a predefined quantity. In other words, the quantity of the dose to be administered is not set or selected with every dispensing operation. Rather, the pen is primed and the dose or quantity pre-set by the construction of the device can then be dispensed.

In one embodiment, the present invention comprises an injection device comprising at least one of an adjusting element and a filling element; a lock comprising a first locking element and a second locking element, the lock allowing a motion of the adjusting and/or filling element in a release position and preventing the motion in a locked position; and a piston rod comprising a trigger element that brings one of the lock elements into interaction with the other lock element thereby creating the locked position.

In one embodiment, the present invention comprises an injection device having a safeguard for preventing a filling or adjusting motion of the injection device when a prescribed dispensing motion has been performed, the injection device comprising an adjusting element and/or a filling element, a blocking mechanism (which also might be thought of and/or referred to as a lock or locking mechanism) comprising a first blocking element and a second blocking element, the blocking mechanism allowing a motion of the adjusting and/or filling element in a release position and preventing the motion in a blocking position, and a piston rod comprising a trigger element that can bring one of the blocking elements into interaction with the other blocking element thereby creating a blocking position at a prescribed insertion position to cause a blocking of at least one of the adjusting element and/or the filling element.

Normally, only one dose is set by a fixed-dose pen which, in the case of a cross-shaped threaded rod with four axially extending grooves, corresponds to a one-quarter rotation of the threaded rod. Unless stated otherwise in this description, such pens may operate on the basis of the principle described in patent specification DE 10 2005 044 096 A1 (see also US Publication numbers US 2007016142 and US 2008183138), the disclosure of which is incorporated herein by reference.

With regard to one embodiment, an injection device in accordance with the present invention is designed so that dispensing operations can be prevented or avoided when the device is empty. In some embodiments, the injection device is designed so that a user of the injection device does not or is not able to effect a setting and priming movement, such as extracting and retracting a button, which would normally be followed by a dispensing movement without a dose actually being dispensed from the injection device.

In one embodiment, the present invention relates to an injection device having a safeguard for preventing a filling or adjusting motion of the injection device when a prescribed dispensing motion has been performed, having an adjusting or filling element; a blocking mechanism having a first blocking element and a second blocking element allowing a motion of the adjusting or filling element in a release position, and blocking said motion in a blocking position, and having a piston rod on which a block trigger element is provided that can bring one of the blocking elements into a blocking position at a prescribed insertion position, to bring about a blocking of the adjusting element or the filling element in interaction with the other blocking element.

In some embodiments, an injection device in accordance with the present invention has an operating element, such as a button, which is pulled out of the injection device to prime the injection device and pushed back into the injection device to initiate or administer an injection. In some embodiments, the operating element is coupled with a priming element such as a rotating sleeve, for example. In this respect, the button may be coupled with the priming element or rotating sleeve in such a way that the button can be extracted without rotating relative to the housing of the injection device, and the rotating sleeve is therefore mounted in the button so that it is able to rotate relative to the button during the extraction operation. The rotating movement of the rotating sleeve may be caused by a threaded engagement or coupling with the injection device. In some embodiments, a retainer, catch and/or snapper element is provided on the priming element and on the injection device for example, which causes the operating element or the button or the priming element coupled with the operating element to be firmly secured or latched after travelling a structurally predefined or adjustable priming distance. This being the case, the retaining or catch mechanism is disposed so that locking or latching does not take place until a sufficiently long extraction distance has been travelled so that dispensing actually takes place when the operating element is subsequently pushed back in during a retraction operation.

In accordance with the present invention, some embodiments of the present invention comprise a priming element and/or operating element coupled with an elastic or spring element, which is non-displaceably coupled with the injection device or a part of it. Thus, a user extracted operating or priming element is pulled back into an initial position by the elastic or spring element, in other words is automatically pushed back into the injection device if a user has initiated but not fully completed the priming movement and/or the priming operation has not been effected in such a way that the predefined priming distance mentioned above has been travelled to the point where latching takes place.

If a user lets go of the operating or priming element before latching or locking takes place following extraction across the predefined minimum extraction distance, the priming and/or operating element is automatically pulled back into the injection device after the user lets go of it, so that a user can not have the impression that an injection has been administered. Since the priming operation usually takes place before the injection device is applied in readiness for administering an injection and the operating element is therefore also pulled back or retracted with the injection device in the non-applied state, a user will realise that a dose was not set and an injection was not administered and will then initiate another attempt at priming.

This ensures that a user can not effect any control operation with the injection device which might mistakenly lead him or her to assume that it has led to an actual injection when a dispensing operation has not, in fact, taken place.

In some embodiments, the operating element and/or a priming element coupled with the operating element may be retained by a releasable retaining or catch element, such as a snapper bead locating in a snapper groove, in which case a certain minimum force needs to be applied by a user when pulling on the operating or priming element to release the retaining or latching connection. In some embodiments, the lock or latch is not released unless a predefined minimum force of 5, 10 or 20 Newton or more, for example, is applied to extract the operating or priming element. When a user applies the minimum force, the operating element is extracted in a saccadic movement on release of the lock to the extent that the injection device is actually fully primed. Following the sudden and saccadic release of the lock holding the operating or priming element, a user is usually not able to reduce the applied force so suddenly that the minimum extraction distance needed to fully prime the injection device is not covered. Releasably securing or locking the priming or operating element by firstly applying a predefined minimum force therefore ensures that the injection device is always fully and correctly primed, thereby enabling dispensing operations to be prevented when empty.

The elastic or spring element which ensures that the non-latched operating element or priming element is retracted again if it has not been fully extracted may be a compression spring of a type known per se. In some embodiments, it is supported on the injection device or a part fixedly connected to the housing at one end and is supported on the operating or priming element at the oppositely lying spring end, such as a projection or stop of the priming element. In some preferred embodiments, the elastic or spring element is disposed between a projection or stop of the injection device and a projection or stop of the priming element or operating element, for example, so that the elastic or spring element is compressed when the operating or priming element is extracted. The compressed spring tensed in this manner ensures that the priming element or operating element is automatically pushed back in if the priming or tensing operation is not fully completed.

Alternatively or in addition, the spring element may also be provided in the form of a tension spring, in which case the spring is tensed during the priming operation and automatically rebounds if the priming or operating element is not latched in the extracted position, causing it to be pushed back in automatically.

In some embodiments, the elastic or spring element can be fixedly connected to the elements mentioned above.

Alternatively or in addition to the elastic or spring elements described above, which act in the longitudinal direction of the injection device, the spring element may also act in a different direction, e.g. radially with respect to the longitudinal axis of the injection device. For example, action may be applied to the side or in the radial direction on a groove or a web of a rotating element which is mounted in a thread pitch during an extraction operation and causes the backward rotating movement.

In one embodiment, the priming element, such as a rotating sleeve, may be mounted in a threaded engagement with the injection device, for example in a threaded sleeve. The thread pitch may be bigger or smaller than the thread pitch of a threaded rod which produces the forward stroke of a stopper. As will be explained in more detail below, a rotating movement of a tensed priming element caused by priming the operating element is transmitted to the threaded rod as the operating element is pushed in, being guided in a guide, such as a guiding sleeve, with the same or a different thread pitch. An increase or decrease in the ratio of the priming movement can therefore be achieved.

Based on another aspect, the present invention further relates to a method of priming an injection device, wherein a resetting element such as an elastic or spring element is acted on by the action of pulling an operating element out of the injection device. In other words, the resetting element is extended, tensed, pushed or compressed to generate a rebounding force in the direction opposite the priming direction so that the operating element is pushed back into the injection device again, in some preferred embodiments automatically, if the operating element or a part coupled with or connected to it is not latched or locked in a final extracted position.

Based on yet another aspect, the present invention relates to a method of priming an injection device, wherein the operating element or a priming element coupled with it is held in a releasable lock which is not released until a minimum tension force has been applied, the saccadic release being intended to ensure that the operating or priming element is completely extracted across a predefined minimum distance.

Based on another aspect of the present invention, it relates to an injection device with a lock for preventing a priming or setting movement of the injection device if a predefined dispensing movement or a predefined number of dispensing movements or dispensing operations have been effected, especially if the plunger rod or threaded rod has travelled a predefined distance in the injection device.

In some embodiments, an injection device in accordance with the present invention has a setting or priming element, such as a button which can be pulled out of the injection device. A lock mechanism is also provided, with a first lock element and a second lock element which do not prevent a priming or setting movement when the priming or setting element is in an initial position. In some embodiments, one of the lock elements by which the plunger rod which is pushed into the injection device during one or more operations for dispensing a substance is moved into a position so that it can co-operate with the other lock element to prevent the setting or priming element from being primed or moved out again.

In some embodiments, a plunger rod or threaded rod associated with the injection device has a lock triggering element, such as a projecting cam or an inclined surface, which, when the plunger rod or threaded rod is in a predefined position, e.g. completely or almost completely pushed in or screwed in, forces, moves or pushes at least one of the lock elements disposed on a plunger rod guide or ratchet sleeve or on a priming element or a rotating sleeve. Thus, it, together with the other lock element fixedly disposed on the injection device blocks or establishes a lock of the setting or priming element or an element connected to it, such as a rotating sleeve.

Providing a lock triggering element on the plunger rod or threaded rod helps ensure that the injection device is locked to prevent further priming once the plunger rod or threaded rod has been pushed so far into the injection device that it can be assumed that a sufficient quantity is no longer available for administering another injection.

In one embodiment, the lock mechanism may be designed so that a first lock element is provided in the form of an elastic or snapper arm, which is disposed radially on the inside of an element in which the plunger rod or threaded rod is mounted, such as a ratchet sleeve. In some embodiments, the element providing a mount for the plunger rod or threaded rod is not able to move axially in the injection device, so that the plunger rod or threaded rod moves relative to this element when a dispensing operation is in progress. As a result, the lock triggering element, e.g. a wider region with an inclined surface, disposed on the plunger rod or threaded rod, e.g. at the end of the plunger rod or threaded rod, is moved by the retracted plunger rod into a position in which it triggers or moves the lock element, e.g. pushes it outwardly in a radial direction.

As a result, the lock element is moved into a position in which it lies against a stop of a setting or priming element and, thus, prevents the setting or priming element from being rotated and/or extracted. For example, a snapper arm of a ratchet sleeve biased radially inwardly can be pushed outwardly by a projection on the end of a threaded rod and lies against a stop of a rotating sleeve connected to a button, thereby preventing the rotating sleeve and the button connected to it from rotating and thus being screwed out or pulled out.

Alternatively or in addition, a lock mechanism based on another embodiment may be provided in the form of an elastic or snapper element of the priming element itself, for example a snapper arm of a rotating sleeve biased radially inwardly. The elastic element is moved by the lock triggering element, for example a projecting cam of the plunger rod or threaded rod, from a release position permitting a setting or rotating movement into a locking position, for example by locating in an element of the injection device such as the housing or a threaded sleeve. The[1] lock element moved out of the priming element can then lie against a stop of the injection device or a threaded sleeve, thereby preventing a rotating movement of the thread-guided priming element and blocking or locking the operating element connected to the priming element so that it can not be extracted.

Based on another aspect, the present invention relates to a method of preventing the priming or setting movement of the injection device if one or more dispensing operations or dispensing movements have already been effected, in which case an operating element or a priming element connected to the operating element is locked or blocked by a lock triggering element, e.g. an inclined surface or a projection of the plunger rod or threaded rod, to prevent an extraction or rotating movement of the operating element or priming element.

BRIEF DESCRIPTION OF THE DRAWINGS

FIG. 4A is a cross-sectional view illustrating a first embodiment of a lock mechanism for preventing an extracting movement when the plunger rod is pushed in;

FIG. 5 illustrates a second embodiment of a lock mechanism for preventing a priming movement when the plunger rod is pushed in.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1:
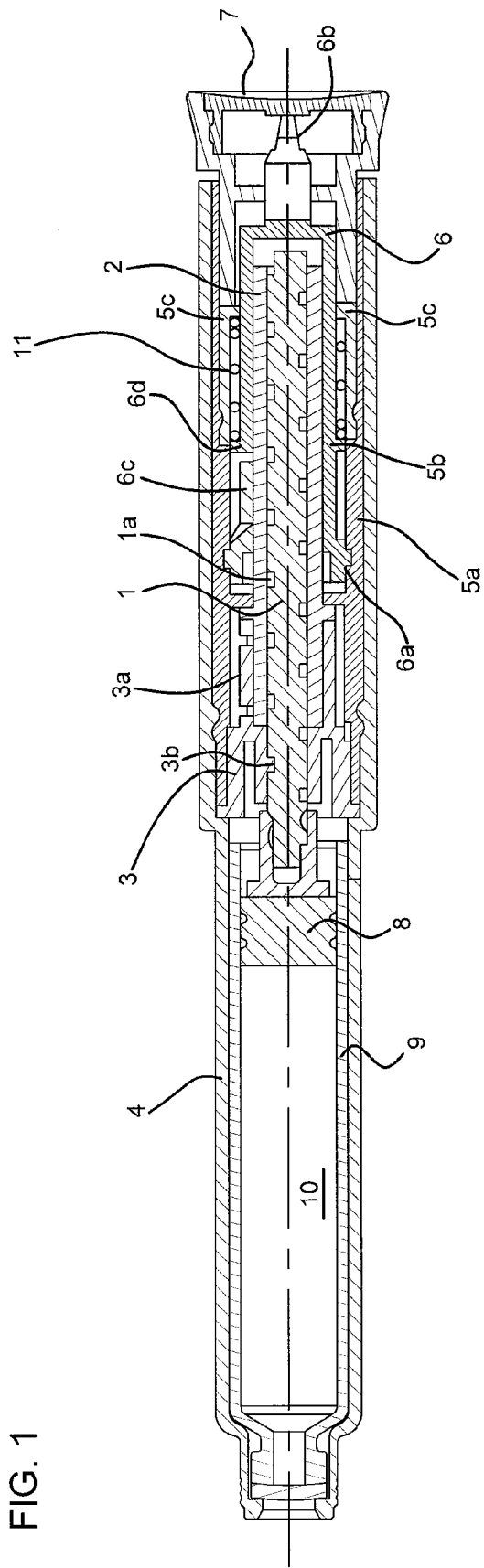
FIG. 1 is a cross-section illustrating a first embodiment of the present invention.
Figure 2:
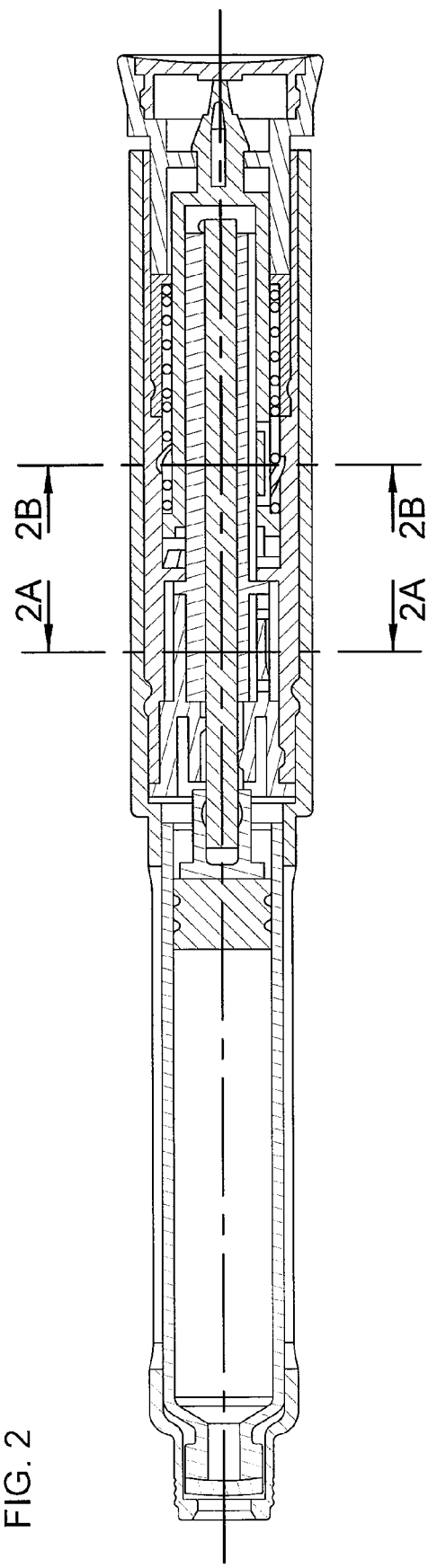
FIG. 2 is a cross-section illustrating a second embodiment of an injection device in an as-supplied the state.
Figure 2B:
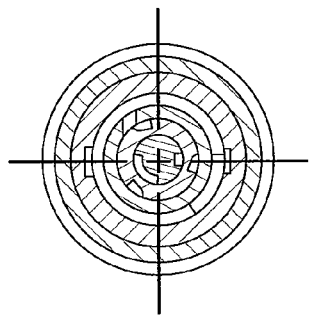
Figure 2A:
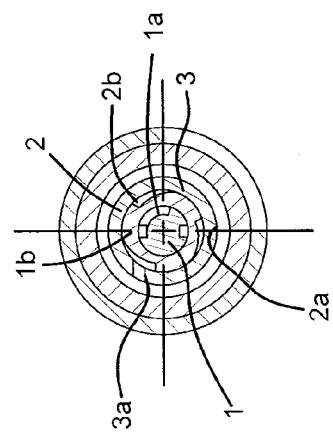

As illustrated in section A-A of FIG. 2, a threaded rod 1 has an external thread 1a and two grooves 1b extending in the axial direction. Two inwardly pointing webs 2a of a ratchet sleeve 2 which can be pushed toward the threaded rod 1 are able to locate in the axially extending grooves 1b. The threaded rod 1 is therefore mounted so that it is not able to rotate relative to the ratchet sleeve 2.

A guiding sleeve 3 is fixedly connected to the pen or pen housing 4 and is therefore prevented from rotating. The guiding sleeve 3 has a snapper or snapper arm 3a biased radially inwardly, which is able to locate in one of, for example, three or four catch grooves 2b of the ratchet sleeve 2 disposed on the external face extending in the axial direction. Retained by the guiding sleeve 3 in this manner, the ratchet sleeve 2 can therefore be locked in three or four rotary positions. (More positions could, naturally, be provided.) Disposed on the ratchet sleeve 2 is a snapper bead (not illustrated in the drawing), which is able to snap into a snapper groove on the internal face of the guiding sleeve 3 to secure the ratchet sleeve 2 and prevent it from falling out of the guiding sleeve 3, while simultaneously enabling a rotation of the ratchet sleeve 2 inside the guiding sleeve 3.

A threaded sleeve 5 is mounted in the housing 4 so that it is prevented from rotating and has an internal thread 5a, in which an external thread 6a of a rotating sleeve 6 locates. The rotating sleeve 6 has a snapper 6b on its rear or proximal end, onto which snaps a button 7 operated by a user to prime the injection device. The rotating sleeve 6 is mounted so that it can rotate in the button 7 by the snapper connection 6b. When the button 7 is extracted from the injection device 4, it drives with it the rotating sleeve 6, which is therefore screwed out and thus rotated by the mounting of the external thread 6a of the rotating sleeve 6 in the internal thread 5a of the threaded sleeve 5 during extraction.

The internal thread 5a of the threaded sleeve 5 in which the external thread 6a of the rotating sleeve 6 is guided is provided on a predefined axial length only, for example as only a thread portion with a 360° turn, so that the rotating sleeve 6 can only be extracted or screwed out of the threaded sleeve 5 as far as the predefined axial length. A stop 5b is provided inside the groove of the internal thread 5a of the threaded sleeve 5 to restrict the thread.

Figure 3:
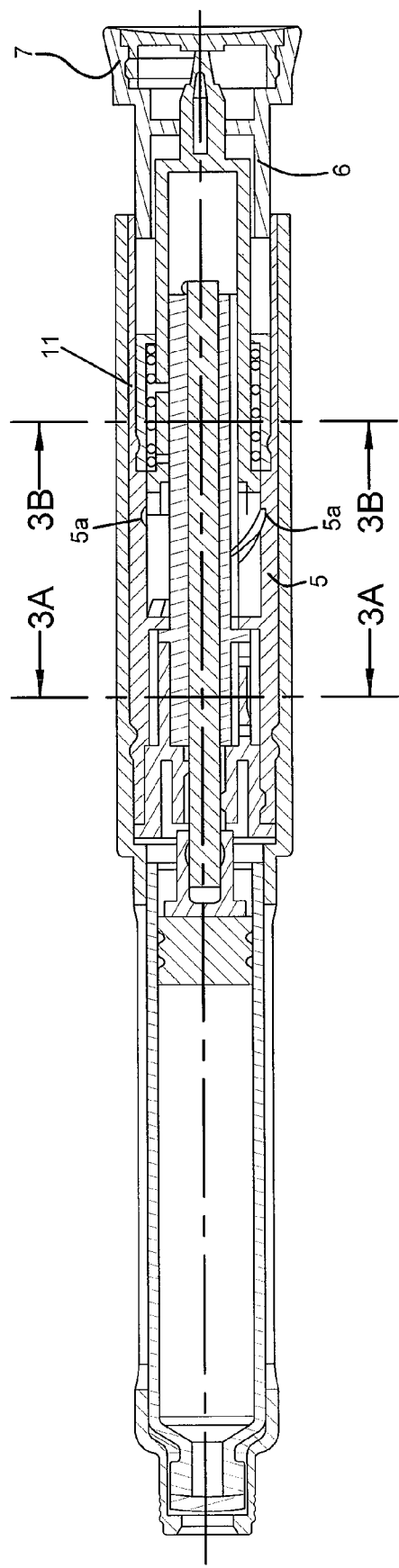
FIG. 3 illustrates an injection device of the type illustrated in FIG. 2 in a primed state.
Figure 3B:
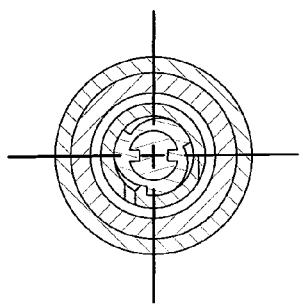
Figure 3A:
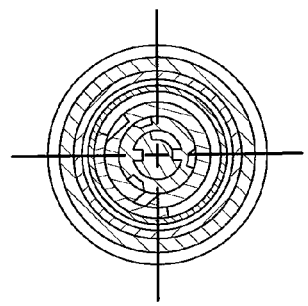

Once the button 7 is extracted, as illustrated in FIG. 3, the pen is charged or fully primed. When the button 7 is pushed back into the pen again, the rotating sleeve 6 is screwed in due to the thread guide 5a, 6a in the thread sleeve 5. A snapper 6c of the rotating sleeve 6 biased radially inwardly locates in the ratchet sleeve 2 and turns it, but the ratchet sleeve 2 is not moved axially during the entire operation. Since the threaded rod 1 is mounted in the ratchet sleeve 2 so that it is prevented from rotating, the rotating movement of the ratchet sleeve 2 is transmitted to the threaded rod 1. The threaded rod 1 is mounted with its external thread 1a in an internal thread 3b of the guiding sleeve 3 and is screwed in relative to the guiding sleeve 3 and pushed forward axially or in the distal direction due to the rotation caused by the ratchet sleeve 2, and pushes on a stopper 8 in the ampoule 9 so that a substance 10 contained in the ampoule 9 is forced out of it, thereby causing the substance 10 to be dispensed.

The threaded engagement of the rotating sleeve 6 in the threaded sleeve 5 is used in the priming operation and this thread pitch is greater than the thread pitch of the threaded engagement between the guiding sleeve 3 and threaded rod 1. This therefore enables a reduction in the ratio of the priming movement to be achieved, in other words a relatively large stroke which takes place when priming the injection device by extracting the button 7 is reduced to a relatively smaller stroke or forward movement of the threaded rod 1.

In the situation wherein the button 7 is not fully extracted, a problem can occur in that the snapper 6c of the rotating sleeve 6 biased radially inwardly is not able to locate in the closest axially extending groove 1b of the threaded rod 1, as a result of which the rotating sleeve 6 is turned relative to the threaded rod 1 but does not drive the threaded rod 1 in rotation with it when the button 7 is pushed back in. A user might therefore be under the impression that this has caused dispensing but in fact the threaded rod 1 was not moved in the axial direction even though the button 7 was extracted from the injection device 4 by a certain distance and pushed back in again.

To address this problem, a compression spring 11 is provided, which is disposed between a radially projecting stop 6d of the rotating sleeve 6 and a radially projecting stop 5c of the threaded sleeve 5 or an element connected to the threaded sleeve 5. During a priming movement, i.e. as the button 7 is being extracted, the compression spring 11 therefore pushes in the direction opposite the priming direction, i.e. forward or in the distal or delievery direction of the injection device. If the snapper 6c of the rotating sleeve 6 does not snap into an axially extending groove 1b of the threaded rod 1 during the priming operation, this compression spring 11 causes the button 7, after it has been released, to be pushed automatically back into the injection device by the compression spring 11 together with the rotating sleeve 6. A user therefore no longer has the feeling or impression that the pen has dispensed.

As an alternative to this solution, the button 7 or rotating sleeve 6 could be mounted or retained in the injection device by a latching action in such a way that a predefined minimum force is needed to release this latching action to extract the button 7 or rotating sleeve 6. When this minimum force is applied, the button 7 is "automatically" pulled out of the injection device across the predefined minimum distance when this latching or retaining action is suddenly released because the jolt which takes place on release of the latching action can not usually be halted by a user.

As the rotating sleeve 6 is being screwed out, the threaded rod 1 is retained by the snapper 3a of the guiding sleeve 3. When the rotating sleeve 6 is pushed in, the snapper 6c of the rotating sleeve 6 retains the threaded rod 1, which is able to rotate due to the snapper 3a of the guiding sleeve 3.

As an alternative or in addition to using a compression spring 11, each of the grooves 2b extending in the axial direction on the external face of the ratchet sleeve 2 may have or comprise an incline so that when the snapper arm 6c of the rotating sleeve 6 is disengaged from the groove 2b of the ratchet sleeve 2, the snapper arm 6c is automatically moved back or rotated back into the initial position relative to the ratchet sleeve 2 due to the clamping force directed radially inwardly. In other words, when the rotating sleeve 6 is turned relative to the ratchet sleeve 2, the snapper arm 6c of the rotating sleeve 6 would generate an opposing or rebound force until the snapper arm 6c has been completely moved out of the groove 2b of the ratchet sleeve 2 and has latched in the next groove 2b in the circumferential direction, thereby restoring the rotating sleeve 6 to a stable state relative to the ratchet sleeve 2. In this case, the compression spring 11 described above can be dispensed with.

The fixedly predefined dose can be varied by varying the pitch of the internal thread 3b of the guiding sleeve 3. If this pitch is made steeper, a bigger dose can be dispensed.

As an alternative, the distance in the circumferential direction between the axially extending catch grooves 2b of the ratchet sleeve 2 could be varied to change the fixedly predefined dose quantity for a predefined thread pitch of the guiding sleeve 3. This being the case, the priming angle of the rotating sleeve 6 must also be varied and set to suit the catch grooves.

Figure 4A:
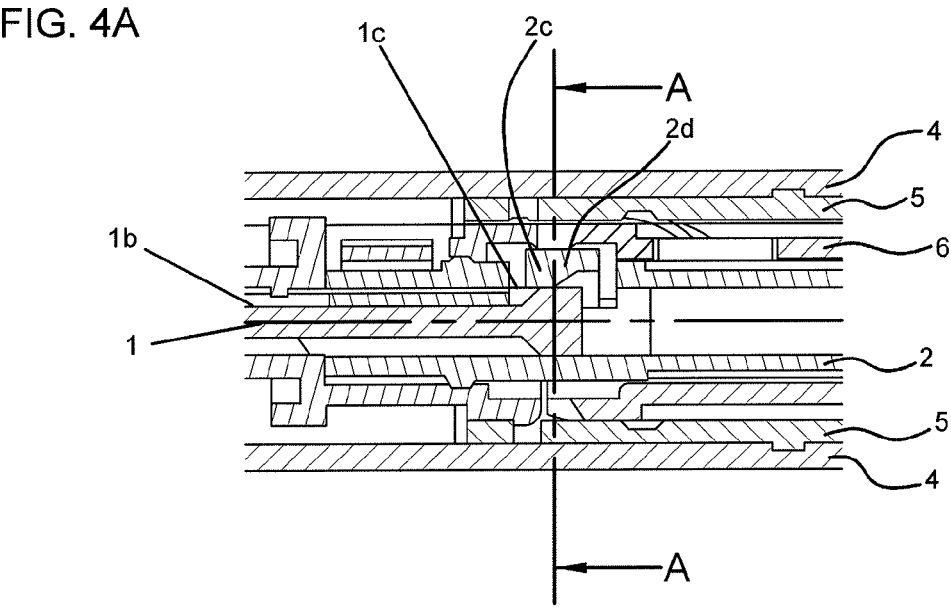
Figure 4B:
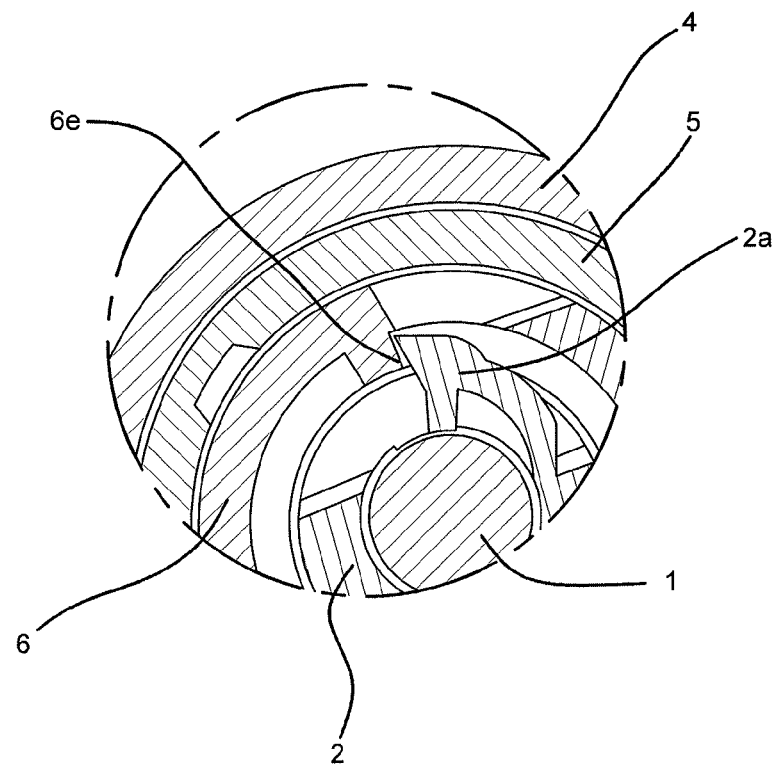
FIG. 4B is a cross-sectional view along line A-A indicated in FIG. 4A.

In one embodiment, which may be thought of and/or referred to as a last dose embodiment, and which may be used independently from or in combination with the embodiments described above, a snapper 2c is provided on the ratchet sleeve 2, as illustrated in section A-A shown in FIG. 4. The snapper 2c does not protrude beyond the ratchet sleeve 2 normally, i.e. when the threaded rod 1 has not yet been fully retracted. The threaded rod 1, which has to be pushed in the distal direction (to the left in FIG. 4A) during a dispensing operation, has an inclined surface 1c at the rear end of an axially extending groove 1b, which causes the snapper arm 2c of the ratchet sleeve 2, which has an inclined surface 2d pointing outwardly in the proximal direction, to be pushed radially outwardly by this inclined surface 2d on the rear end of the axially extending groove 1b of the threaded rod 1 when the threaded rod 1 is fully retracted into the ratchet sleeve 2.

The rotating sleeve 6 has a restrictor element 6e pointing radially inwardly and the snapper arm 2c of the ratchet sleeve 2 is moved so that it rests against it when extracted. In this state, it is no longer possible to pull out the button 7 because the button 7 connected to the rotating sleeve 6 can no longer be pulled out due to the resultant lock preventing the rotating sleeve 6 from being turned further.

Figure 5:
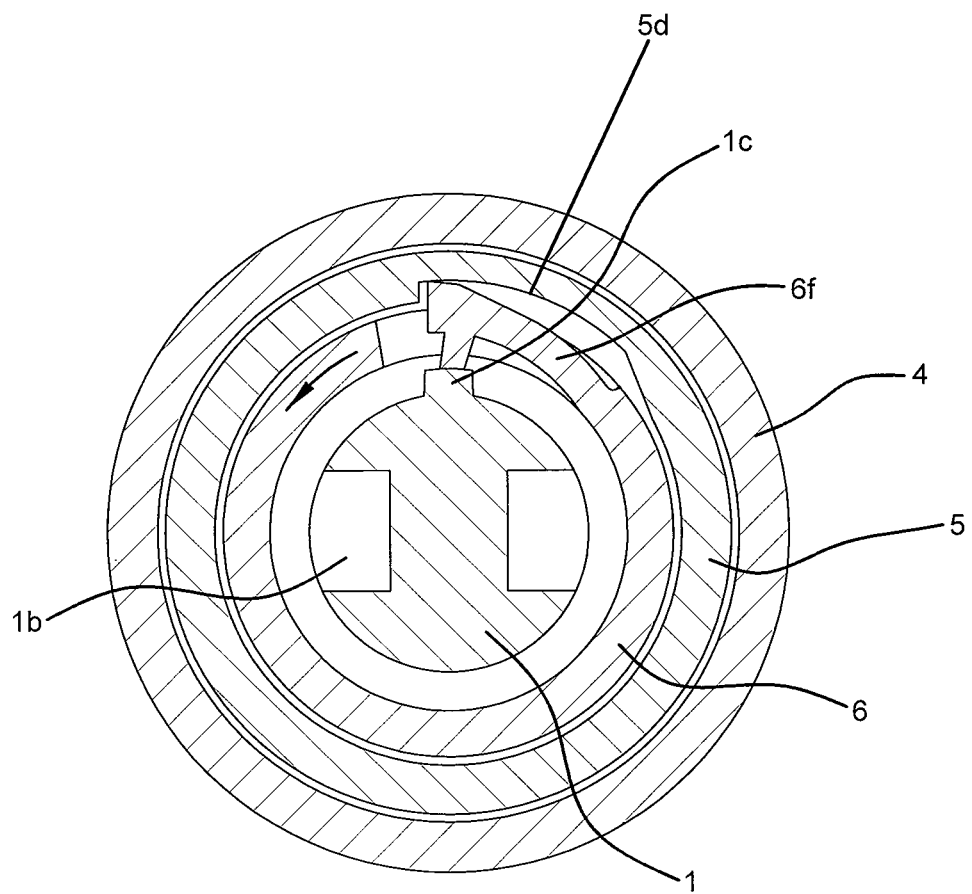

Generally speaking, this last dose principle may also be used with a pen or ratchet sleeve 2 of the type illustrated in FIG. 5, where a catch arm 6f of the rotating sleeve 6 can be pushed outwardly by a threaded rod 1 of the design described above when the threaded rod 1 is fully retracted, for example to latch the rotating sleeve 6 fixedly to the threaded sleeve 5, for example in an inwardly lying cut-out or recess 5d of the threaded sleeve 5 or the pen. This will prevent a further priming movement or extraction of the button 7.

A "last dose" lock of the type described herein and the concept of the compression spring 11 described herein may be used with any known fixed-dose pen.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising a lock to prevent a priming or setting movement of the injection device when a predefined dispensing movement has been effected, the injection device comprising a setting or priming element, a lock mechanism with a first lock element and a second lock element which permit a movement of the setting or priming element in a release position and prevent it in a locked position, and with a plunger rod on which a lock triggering element is provided which is able to move one of the lock elements into a locking position in a predefined retraction position to establish a lock of the setting or priming element in co-operation with the other lock element, wherein in the locked position the first locking element is urged outwardly in a radial direction by the lock triggering element and bears against the second locking element, comprising an abutment on a rotary sleeve of the injection device, and thus prevents movement of the setting or priming element.

2. The injection device as claimed in claim 1, wherein the first lock element is provided on a guide associated with the plunger rod and can be moved by the lock triggering element into a locking position or into engagement with the setting or priming element to lock the setting or priming element to prevent a rotation or movement.

3. The injection device as claimed in claim 1, wherein a lock element is provided on the setting or priming element, which can be moved by the lock triggering element into engagement with or contact with a projection of an element of the injection device or a threaded sleeve associated therewith to prevent a setting or priming movement of the setting or priming element.

4. A method of preventing at least one of a priming movement or setting movement of an injection device when one or more dispensing operations or dispensing movements have been effected, the method comprising the steps of:

locking at least one of an operating element or a priming element connected to the operating element via a lock triggering element which is integral with the operating element to prevent a movement of the operating element or the priming element, wherein in a locked position a first locking element is urged outwardly in a radial direction by the lock triggering element and bears against a second locking element which is an abutment on a rotary sleeve of the injection device, the abutment of the first and second locking elements thus preventing movement of the operating or priming element.

5. The method according to claim 4, wherein the injection device comprises a plunger, and wherein the lock triggering element comprises an inclined surface associated with the plunger.

6. The method according to claim 5, wherein the movement is a rotating movement.

7. An injection device comprising:
a moveable adjusting element;
a lock comprising a first locking element and a second locking element and having a locked state and an unlocked state, the lock preventing movement of the adjusting element in the locked state and allowing movement of the adjusting element in the unlocked state; and
a piston rod comprising a trigger element that moves one of the lock elements into interaction with the other lock element thereby causing the locked state, wherein in the locked state the first locking element is urged outwardly in a radial direction by the trigger element and bears against the second locking element, comprising an abutment on a rotary sleeve of the injection device, and thus prevents movement of the adjusting element.

8. The injection device according to claim 7, wherein the trigger element comprises an inclined surface of the piston rod.

9. The injection device according to claim 8, wherein the injection device performs a dispensing movement and the trigger element moves one of the lock elements into interaction with the other lock element during the dispensing movement.

10. The injection device according to claim 9, wherein in the locked state, the lock prevents movement of the adjusting element after a dispensing movement.

\* \* \* \* \*